(12) United States Patent
Holland et al.

(10) Patent No.: US 9,029,369 B2
(45) Date of Patent: May 12, 2015

(54) APREPITANT L-PROLINE COMPOSITION AND COCRYSTAL

(75) Inventors: Joanne Holland, Cambridge (GB); Christopher Frampton, Stowmarket (GB); Alan Chorlton, Newmarket (GB); Daniel Gooding, Cambridge (GB)

(73) Assignee: Nuformix Limited (GB)

( * ) Notice: Subject to any disclaimer, the term of this patent is extended or adjusted under 35 U.S.C. 154(b) by 234 days.

(21) Appl. No.: 13/825,380

(22) PCT Filed: Sep. 23, 2011

(86) PCT No.: PCT/IB2011/054210
§ 371 (c)(1), (2), (4) Date: Jun. 3, 2013

(87) PCT Pub. No.: WO2012/038937
PCT Pub. Date: Mar. 29, 2012

(65) Prior Publication Data
US 2013/0252949 A1 Sep. 26, 2013

Related U.S. Application Data

(60) Provisional application No. 61/385,744, filed on Sep. 23, 2010, provisional application No. 61/439,654, filed on Feb. 4, 2011, provisional application No. 61/498,214, filed on Jun. 17, 2011.

(51) Int. Cl.
*A61K 31/535* (2006.01)
*C07D 413/06* (2006.01)
*C07D 207/10* (2006.01)

(52) U.S. Cl.
CPC ............ *C07D 413/06* (2013.01); *C07D 207/10* (2013.01)

(58) Field of Classification Search
CPC ..... A61K 31/535; A61K 9/14; C07D 207/10; C07D 413/06
USPC .......................... 514/230.8; 544/132; 424/489
See application file for complete search history.

(56) References Cited

U.S. PATENT DOCUMENTS

| | | |
|---|---|---|
| 5,145,684 A | 9/1992 | Liversidge et al. |
| 5,719,147 A | 2/1998 | Dorn et al. |
| 6,048,859 A | 4/2000 | Dorn et al. |
| 6,096,742 A | 8/2000 | Crocker et al. |
| 6,235,735 B1 | 5/2001 | Dorn et al. |

FOREIGN PATENT DOCUMENTS

| | | |
|---|---|---|
| CN | 1668283 A | 9/2005 |
| WO | 95/16679 A1 | 6/1995 |
| WO | WO 2004/000284 A1 | 12/2003 |
| WO | 2004/078161 A1 | 9/2004 |
| WO | 2009/108828 A2 | 9/2009 |
| WO | 2012/038937 A1 | 3/2012 |

OTHER PUBLICATIONS

Search Report and Written Opinion for PCT International Application No. PCT/IB2011/054210, filed Sep. 23, 2011.
Miroshnyk et al., "Capturing the advantages of co-crystals", Pharmaceutical Technology 22(7):1-8 (2010).
Tilborg et al., "Advantages of cocrystallization in the field of solid-state pharmaceutical chemistry: I-Proline and MnCl2," European Journal of Medicinal Chemistry 45(8):3511-3517 (2010).
Ständer et al., "Targeting the Neurokinin Receptor 1 with Aprepitant: A Novel Antipruritic Strategy," PLoS One 5(6) e10968:1-5 (2010).
Muñoz et al., "The NK-1 receptor antagonist aprepitant as a broad spectrum antitumor drug" Invest New Drugs 28(2):187-193 (2010).
Mantyh et al., "Substance P Receptors: Localization by Light Microscopic Autoradiography in Rat Brain Using [3H]SP as the Radioligand," Brain Research 307:147-165 (1987).
Goodman and Gilman's "The Pharmacological Basis of Therapeutics", Tenth Edition, pp. 155-173 (A. Gilman, J. Hardman and L. Limbird, eds., McGraw-Hill Press, 2001).
Remington's Pharmaceutical Sciences, 18th Ed., Table of Contents (Mack Publishing Company, Easton, Pa., 1990).
International Preliminary Report on Patentability for PCT International Application No. PCT/IB2011/054210, filed Sep. 23, 2011.

*Primary Examiner* — James O Wilson
*Assistant Examiner* — Ebenezer O Sackey
(74) *Attorney, Agent, or Firm* — J.A. Lindeman & Co., PLLC

(57) ABSTRACT

A 1:1:1 aprepitant L-proline $H_2O$ composition and a 1:1:1 aprepitant L-proline $H_2O$ cocrystal are disclosed as well as pharmaceutical compositions containing a 1:1:1 aprepitant L-proline $H_2O$ composition or cocrystal and a pharmaceutically acceptable carrier. The 1:1:1 aprepitant L-proline $H_2O$ composition or cocrystal may be used in the same way as aprepitant to treat or prevent disorders relating to emesis, a neuropsychiatric disease, an inflammatory disease, pairs, cancer, a skin disease, itch, a respiratory disease, or an addiction.

12 Claims, 14 Drawing Sheets

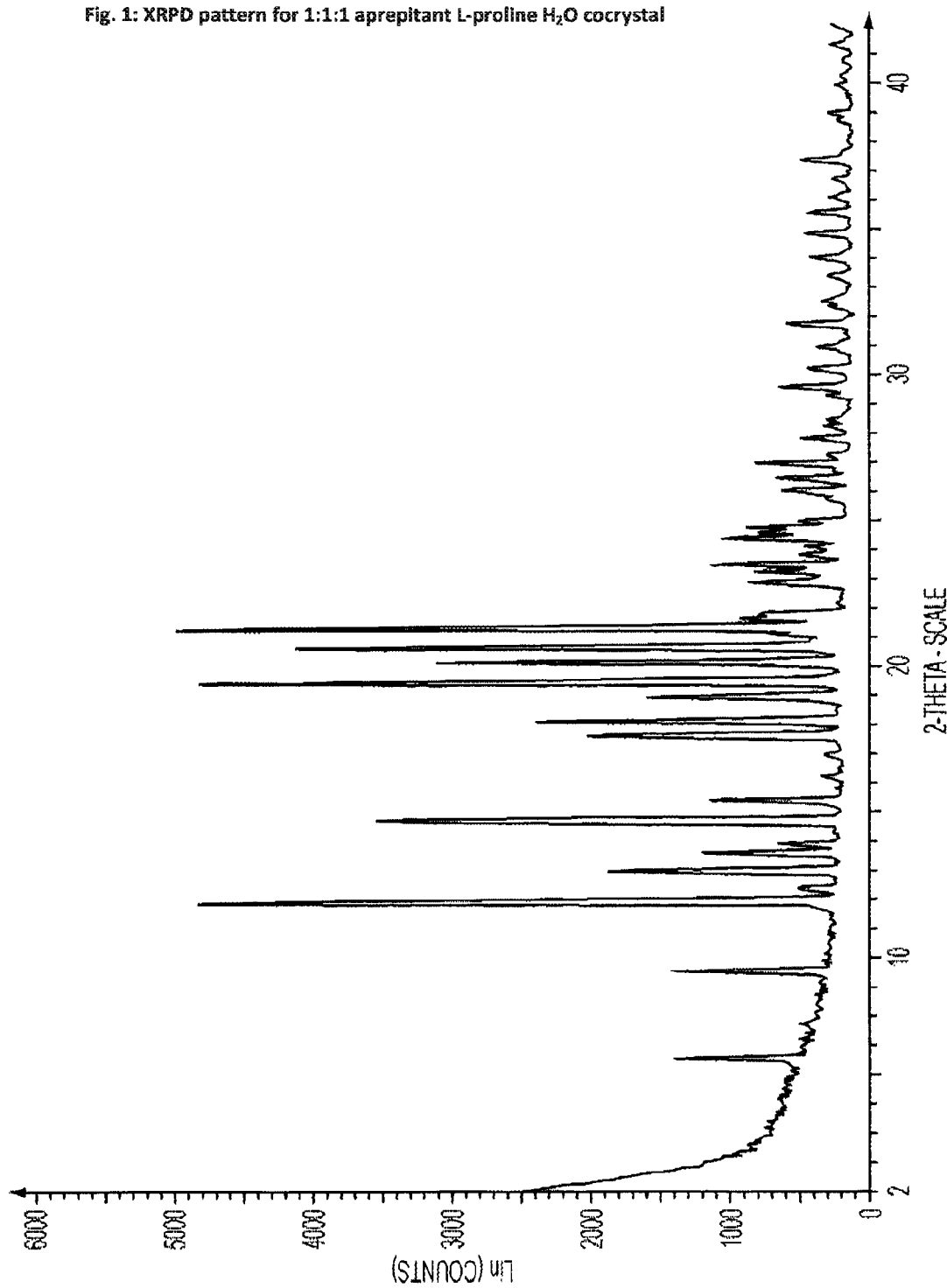

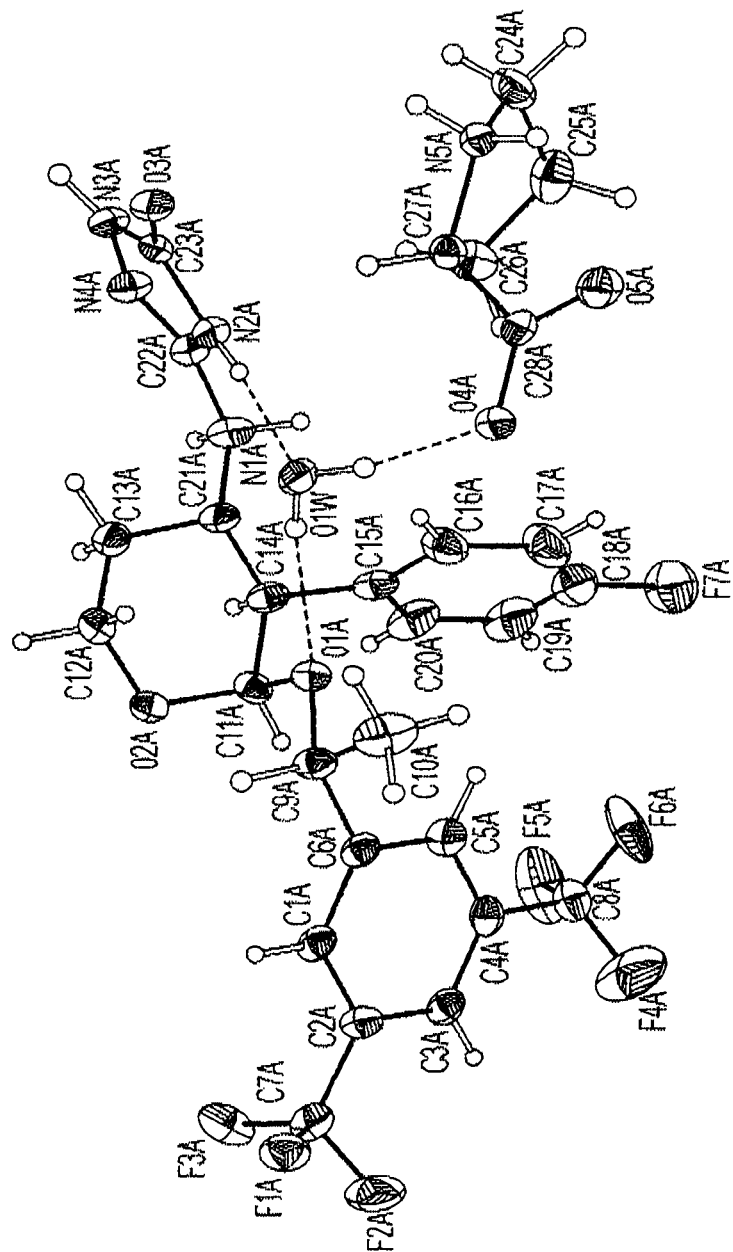
Fig.2: A view of molecule A of the 1:1:1 Aprepitant L-Proline H₂O Cocrystal at 100 K.

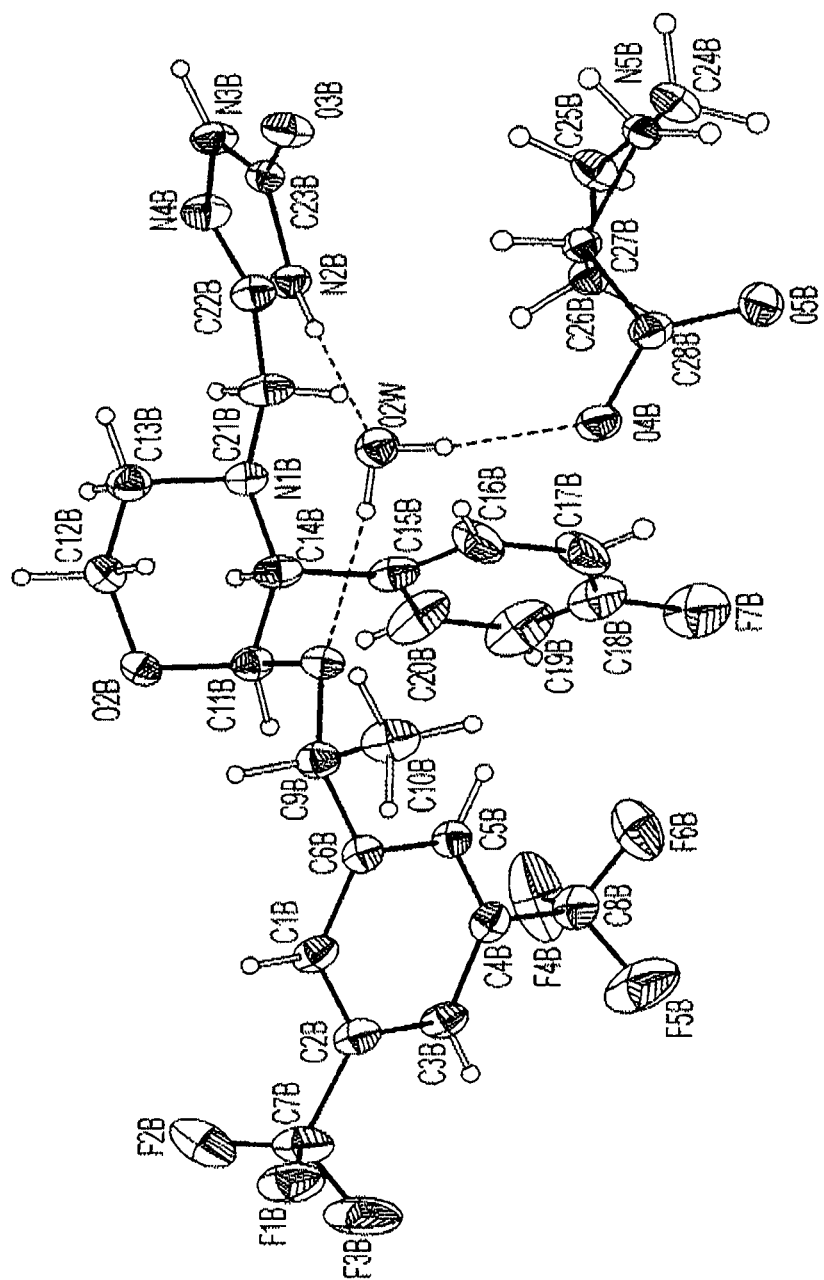
Fig. 3: A view of molecule B of the 1:1:1 Aprepitant L-Proline H₂O Cocrystal at 100 K.

Fig 4: A view of the crystal packing of the 1:1:1 Aprepitant L-Proline H₂O Cocrystal at 100 K down the *a*-axis of the unit cell.
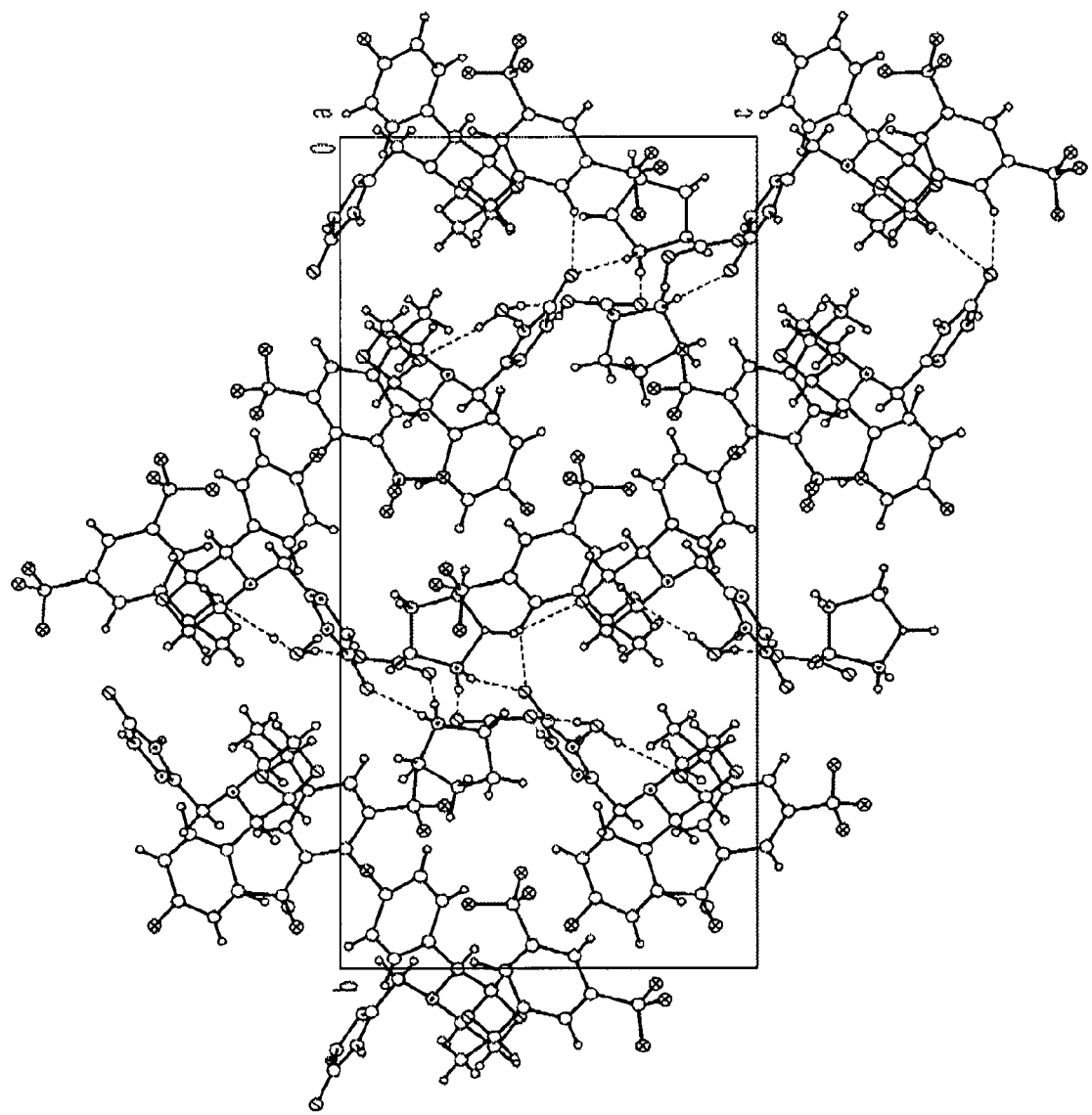

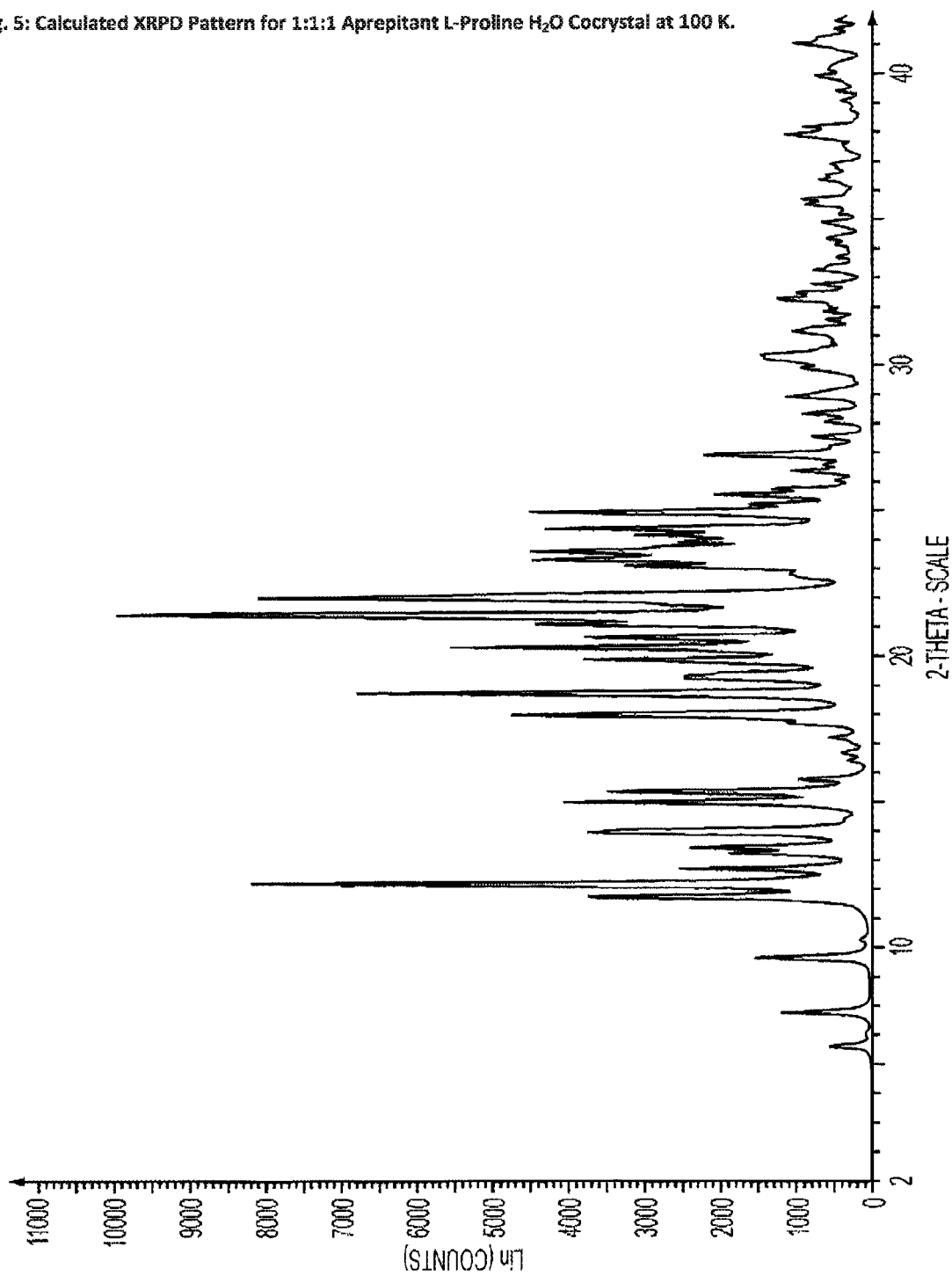
Fig. 5: Calculated XRPD Pattern for 1:1:1 Aprepitant L-Proline $H_2O$ Cocrystal at 100 K.

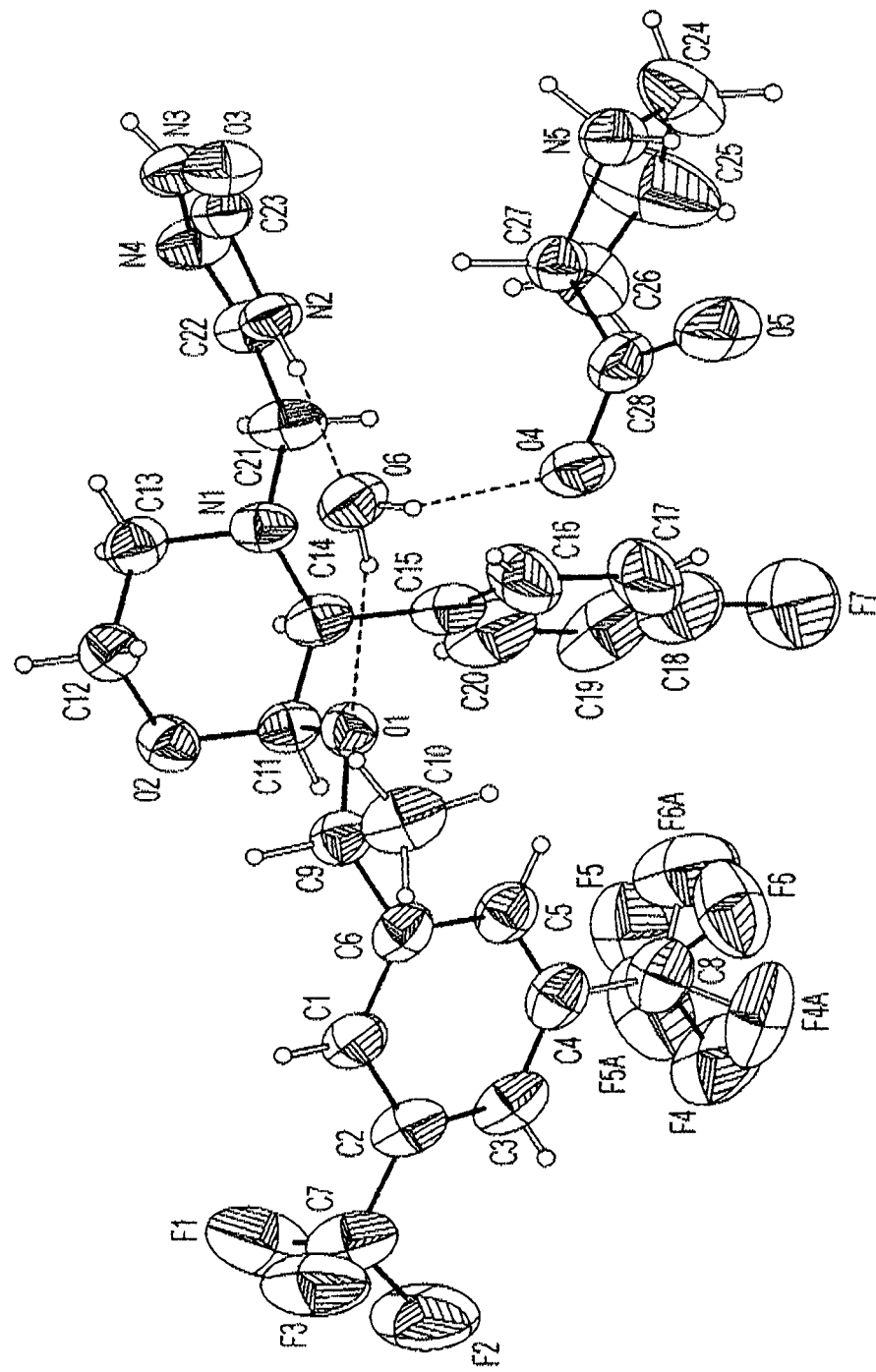
Fig.6: A view of the 1:1:1 Aprepitant L-Proline H₂O Cocrystal at 294 K.

Fig 7: A view of the crystal packing of the 1:1:1 Aprepitant L-Proline H$_2$O Cocrystal at 294 K down the *a*-axis of the unit cell.
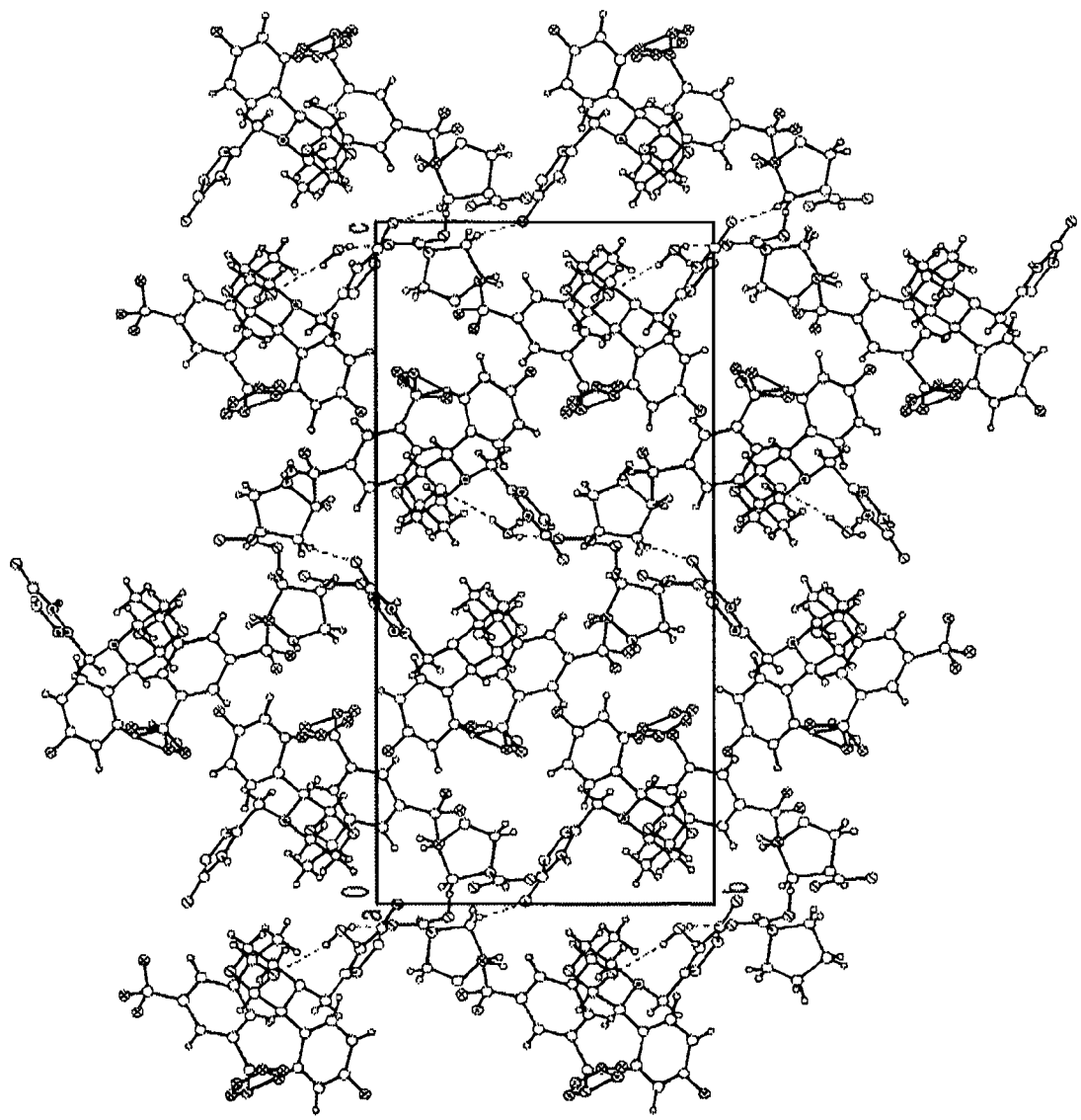

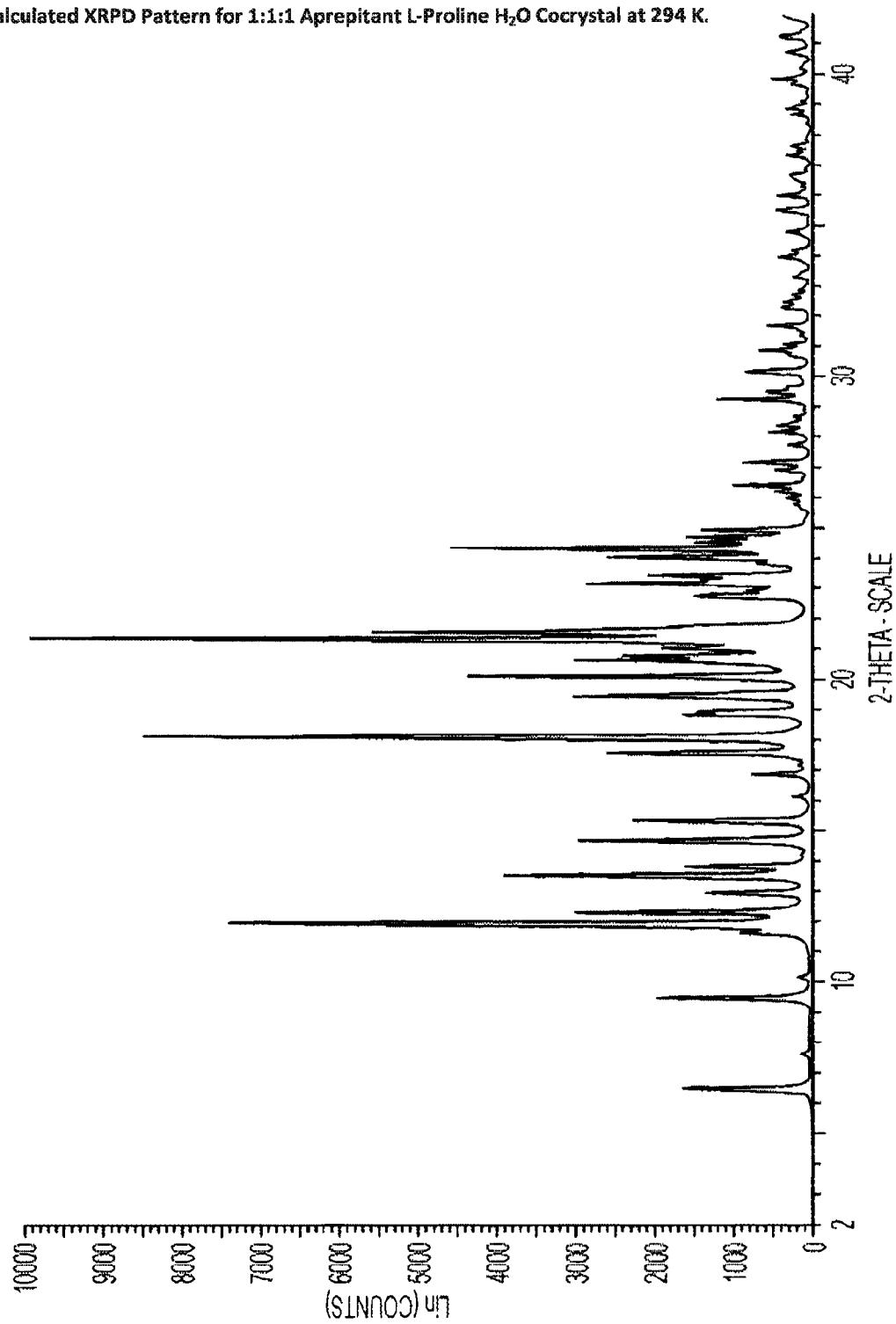
Fig. 8: Calculated XRPD Pattern for 1:1:1 Aprepitant L-Proline H₂O Cocrystal at 294 K.

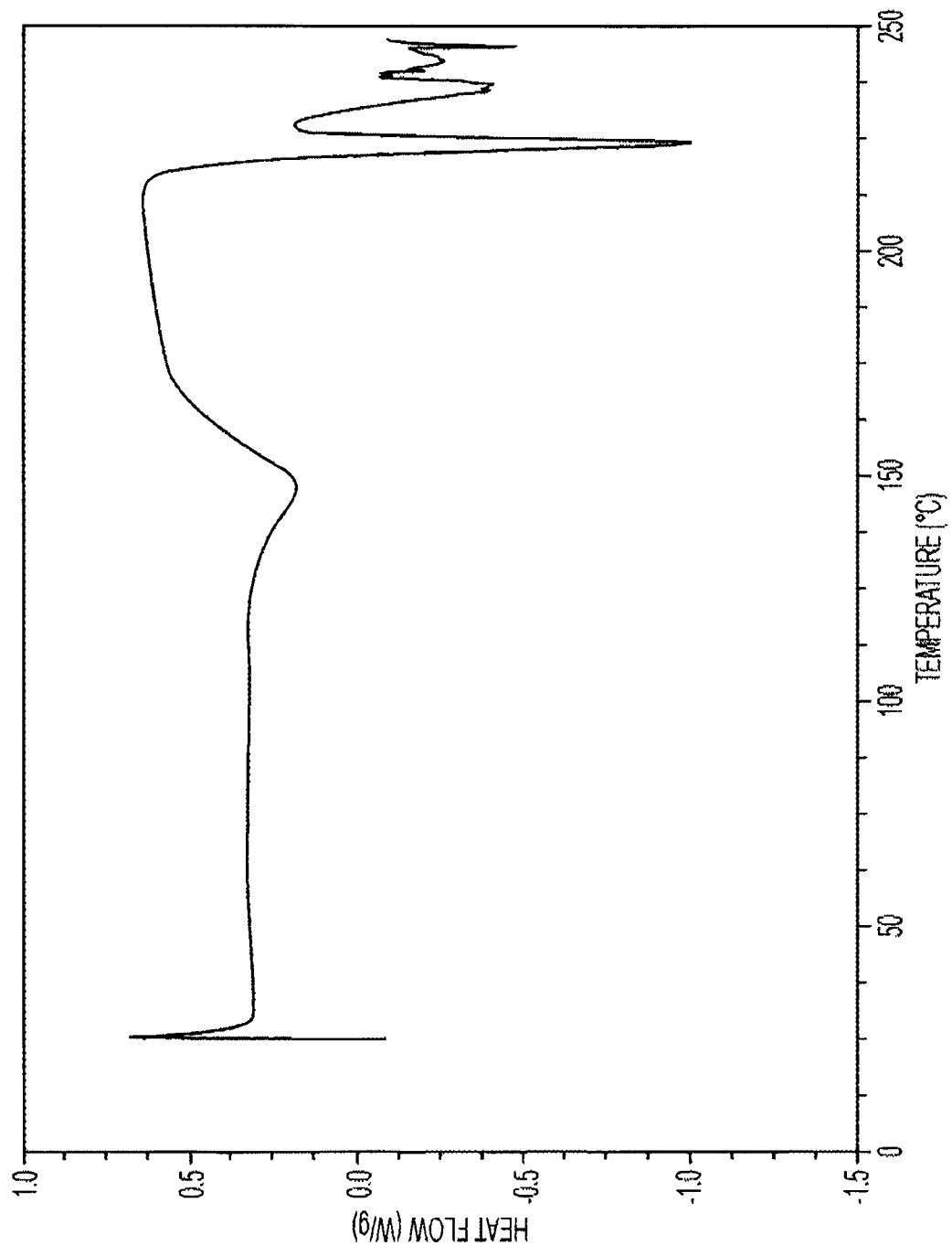
Fig. 9: DSC Trace for a 1:1:1 Aprepitant L-Proline $H_2O$ Cocrystal.

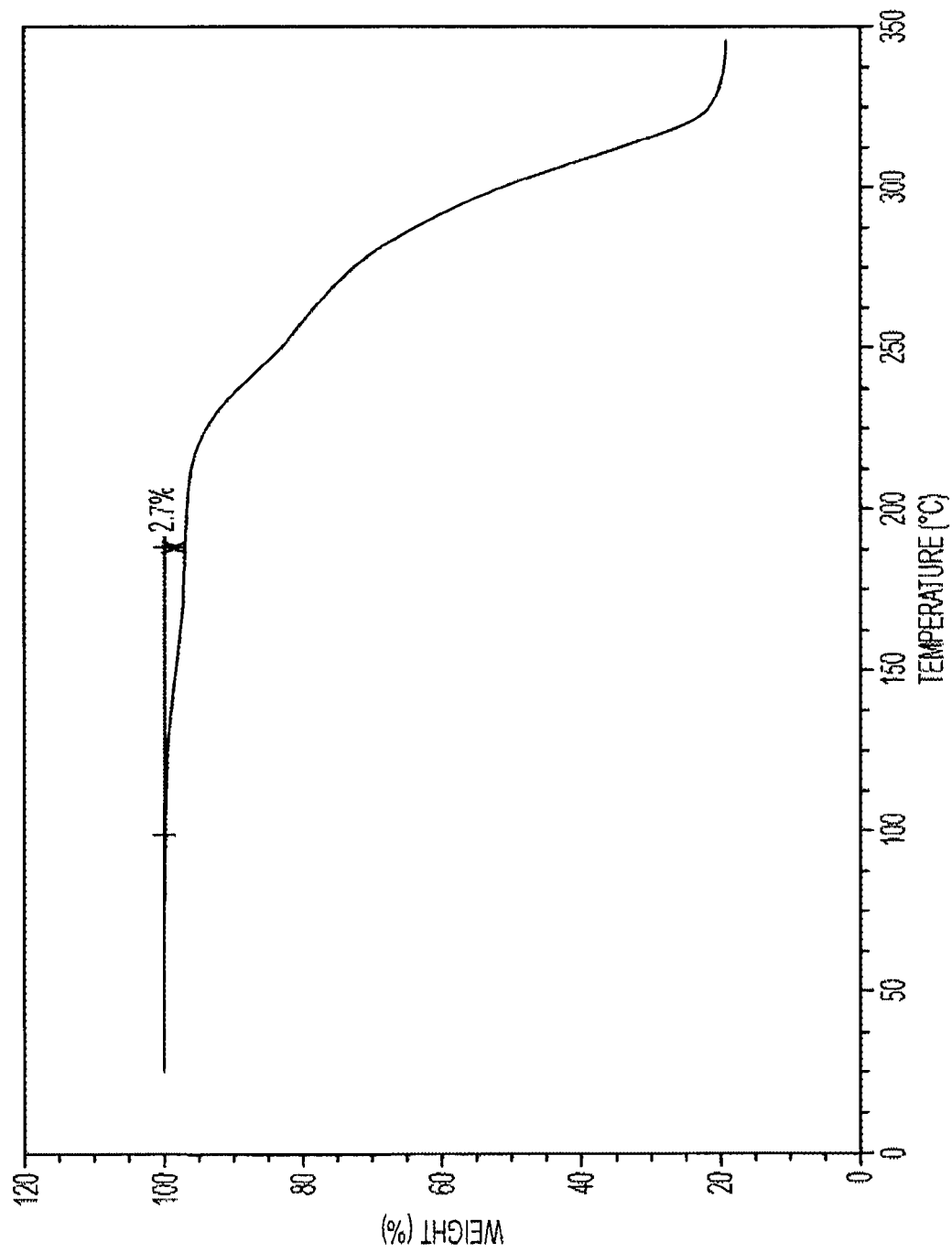
Fig. 10: TGA Trace for a 1:1:1 Aprepitant L-Proline $H_2O$ Cocrystal.

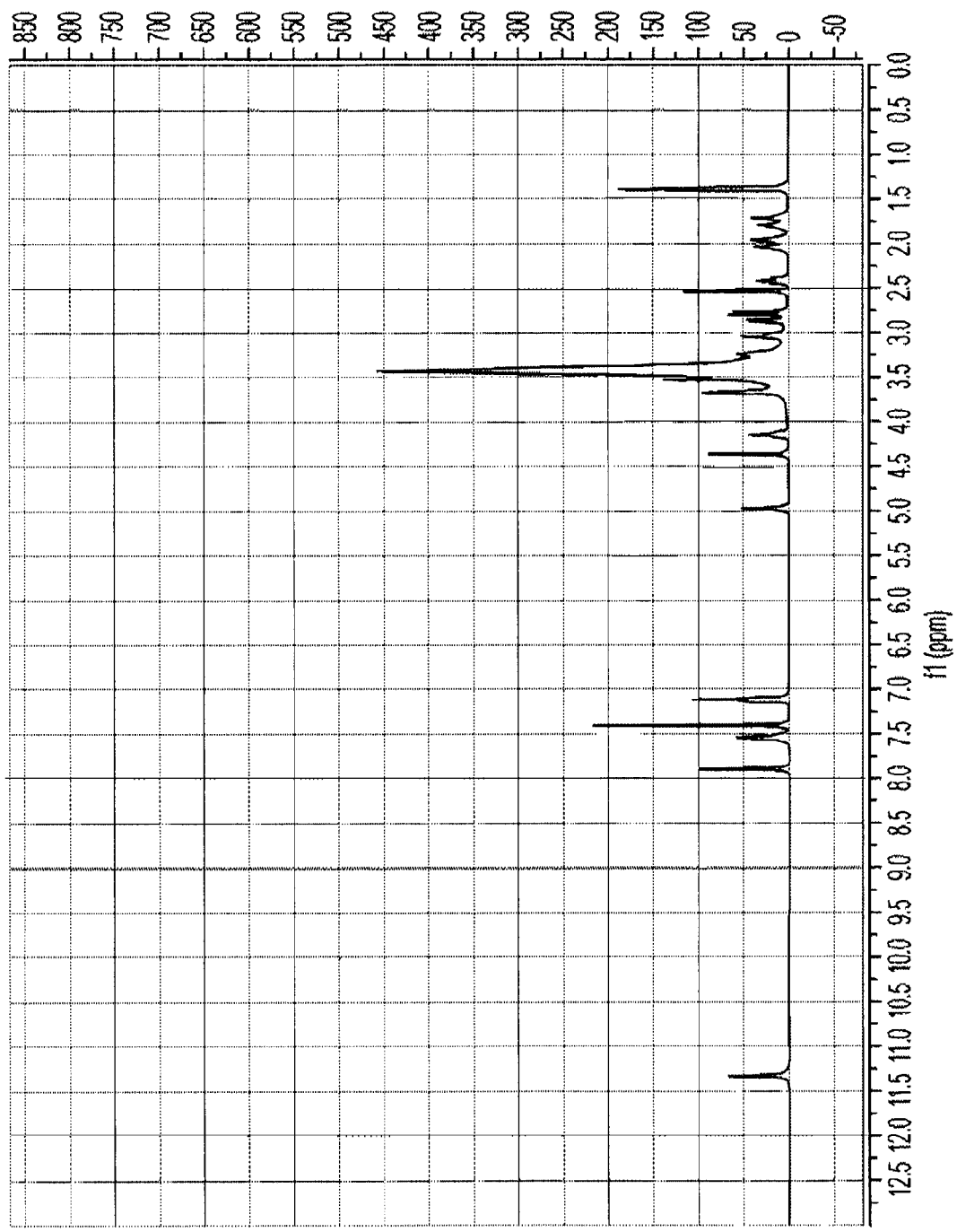
Fig. 11: ¹H NMR Spectrum of 1:1:1 Aprepitant L-Proline H₂O Cocrystal.

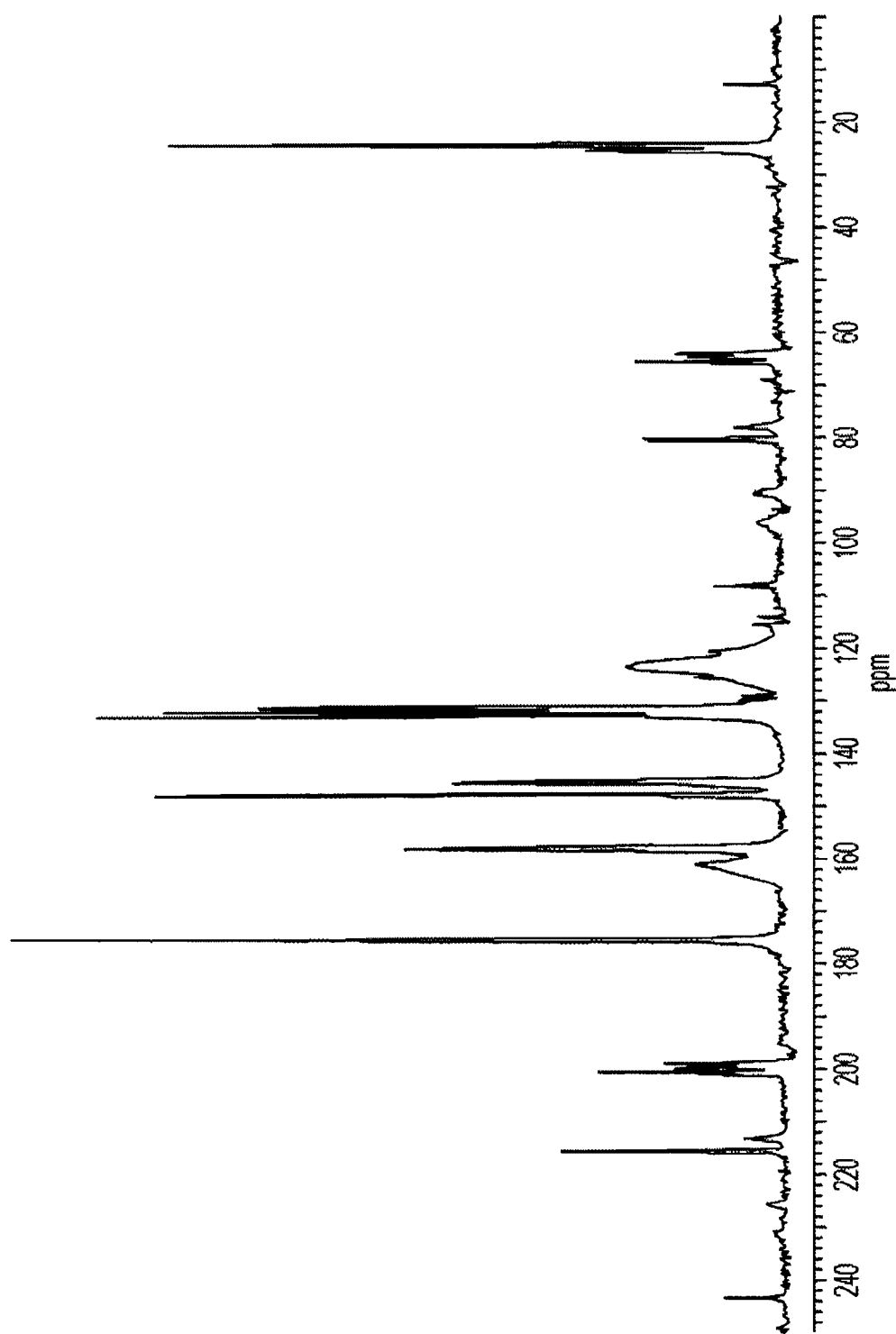
Fig. 12: $^{13}$C Solid State NMR spectrum of 1:1:1 aprepitant L-proline H$_2$O cocrystal using dipolar dephasing.

Fig. 13: Mean dissolution profiles of 1:1:1 aprepitant L-proline $H_2O$ cocrystal and pure aprepitant in distilled water containing 2.2% SDS.
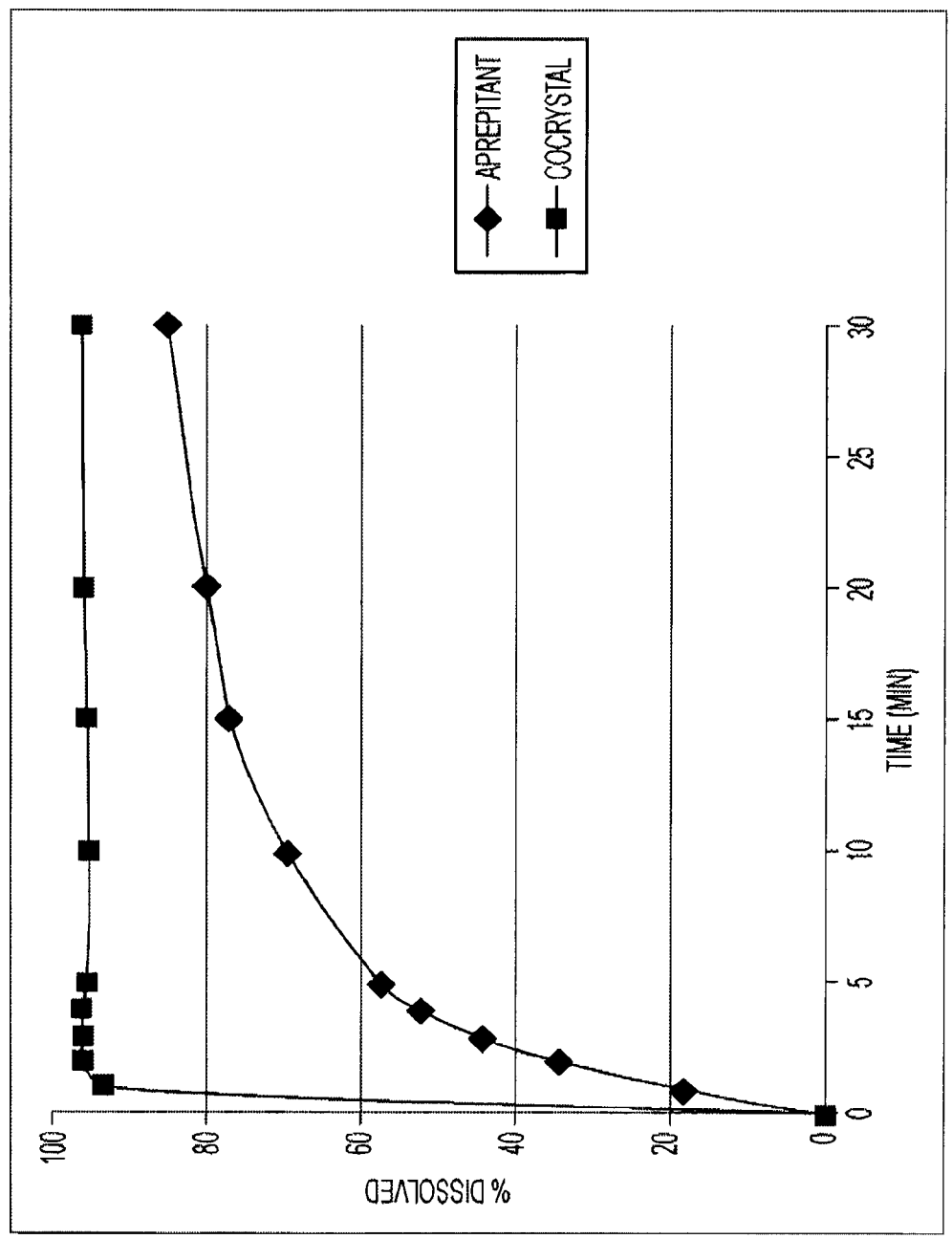

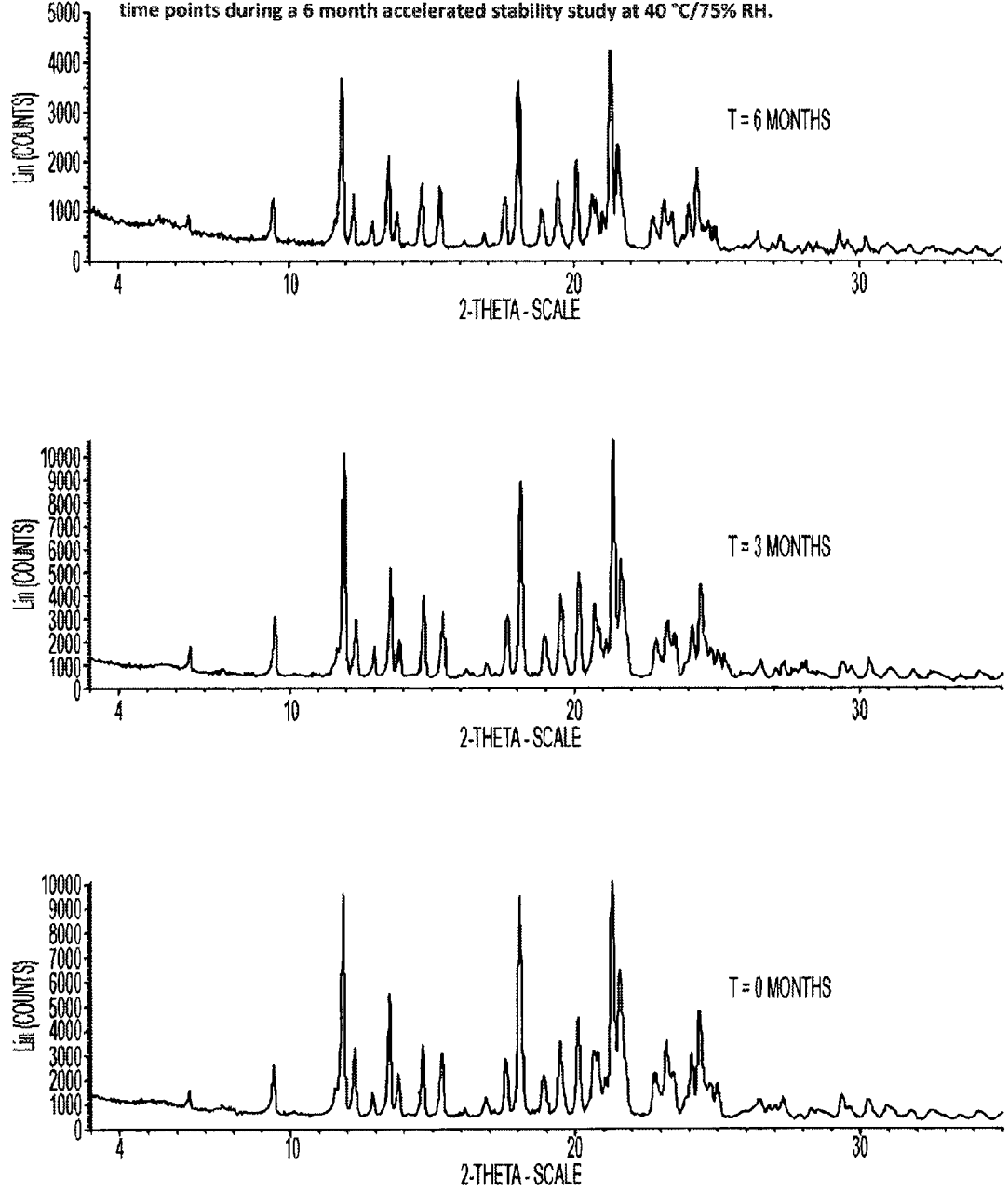
Fig. 14: An overlay of the XRPD patterns of the 1:1:1 aprepitant L-proline $H_2O$ cocrystal at various time points during a 6 month accelerated stability study at 40 °C/75% RH.

APREPITANT L-PROLINE COMPOSITION AND COCRYSTAL

CROSS-REFERENCE TO RELATED APPLICATIONS

Priority is claimed to U.S. Application Ser. No. 61/385,744, filed 23 Sep. 2010; to U.S. Application Ser. No. 61/439,654, filed 4 Feb. 2011; and to U.S. Application Ser. No. 61/498,214, filed 17 Jun. 2011; which disclosures are incorporated herein by reference.

FIELD OF THE INVENTION

The invention relates to a new aprepitant composition and a crystalline compound containing aprepitant, more particularly, the invention relates to an aprepitant L-proline composition, an aprepitant L-proline cocrystal, therapeutic uses of the aprepitant L-proline or the aprepitant L-proline cocrystal, and pharmaceutical compositions containing an aprepitant cocrystal.

BACKGROUND

Nausea and vomiting are commonly experienced by cancer patients in the course of their disease and treatment. Nausea and/or vomiting may be a result of the cancer itself or from its treatment. Aprepitant, 2-(8)-(1-(8)-(3,5-bis(trifluoromethyl)-phenyl)ethoxy)-3-(5)-(4-fluoro)-phenyl-4-(3-(5-oxo-1H, 4H-1,2,4-triazolo)methylmorpholine, shown below, is a substance P/neurokinin 1 (NK1) receptor antagonist used to prevent of acute and delayed nausea and vomiting associated with moderately- and highly-emetogenic chemotherapy and to prevent postoperative nausea and vomiting (PONV).

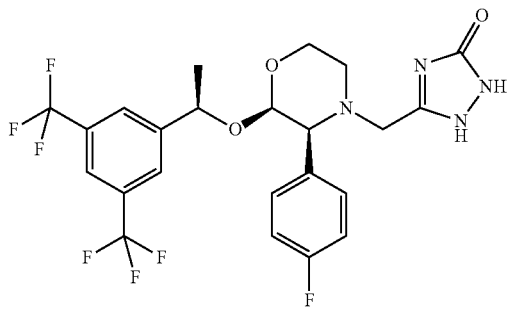 [SMILES: C[C@@H](O[C@H]1OCCN(Cc2nc(=O)[nH][nH]2)[C@H]1c1ccc(F)cc1)c1cc(C(F)(F)F)cc(C(F)(F)F)c1]

The neuropeptide receptors for substance P (neurokinin-1: NK-1) are distributed throughout the mammalian nervous system, the circulatory system and peripheral tissues and are involved in the regulation of a number of biological processes including sensory perception of olefaction, vision, pain, vasodilation, gastric motility and movement control. Substance P antagonists are being studied for their usefulness against neuropsychiatric diseases, inflammatory diseases, pain (including migraine), skin diseases, asthma and other respiratory diseases and emesis. Substance P is known to be a major mediator of pruritus, also commonly known as itch. Studies have reported that aprepitant, as a substance P antagonist, can have a therapeutic effect in the treatment of pruritus (S. Ständen "Targeting the neurokinin Receptor 1 with aprepitant: a novel antipruritic strategy" PLoS One. 2010; 5(6) e10968). The types of itch or skin irritation, include, but are not limited to: a) psoriatic pruritus, itch due to hemodyalisis, aguagenic pruritus, and itching caused by skin disorders (e.g., contact dermatitis), systemic disorders, neuropathy, psychogenic factors or a mixture thereof; b) itch caused by allergic reactions, insect bites, hypersensitivity (e.g., dry skin, acne, eczema, psoriasis), inflammatory conditions or injury; c) itch associated with vulvar vestibulitis; and d) skin irritation or inflammatory effect from administration of another therapeutic such as, for example, antibiotics, antivirals and antihistamines.

It has been demonstrated that NK1 receptors are overexpressed in a wide range of tumor cells and that NK1 receptor antagonists, such as aprepitant, on binding to these receptors can inhibit tumor cell proliferation, angiogenesis and migration of tumor cells. In vitro studies have shown the effectiveness of aprepitant in a range of cancer cell lines including malignant melanoma, neuroblastoma, pancreas, gastric and colon carcinoma cell lines. These studies suggest aprepitant's potential as a broad spectrum anti-tumor drug (M. Muñoz. "The NK-1 receptor antagonist aprepitant as a broad spectrum antitumor drug" Invest New Drugs. 2010 April; 28(2): 187-93).

Substance P has been implicated in the response to stress, as well as reward related behaviours (P. W. Mantyh. Brain Research. 1987; 307: 147-165). Clinical trials are currently ongoing to investigate whether aprepitant, as a substance P antagonist, could have a positive effect on the cravings and dependency associated with addictive substances such as alcohol, cocaine, opioids, cannabis and tobacco.

Aprepitant is classified by the Biopharmaceutical Classification System (BCS) as a Class IV drug, indicating that it is a low solubility and low permeability API. APIs with poor water solubility are usually characterised by low absorption and poor bioavailability. Aprepitant is a white to off-white crystalline solid which is sparingly soluble in ethanol and isopropyl acetate, slightly soluble in acetonitrile but practically insoluble in water. Aprepitant is identified by CAS Registry Number: 170729-80-3. Aprepitant is disclosed in PCT application WO 95/16679 along with a process for its preparation. See also U.S. Pat. Nos. 5,719,147; 6,048,859; and 6,235,735, 6,096,742 describes polymorphic forms of aprepitant.

Aprepitant is currently approved for the prevention of nausea and vomiting associated with chemotherapy and also for the prevention of postoperative nausea and vomiting. It is marketed by Merck & Co., Inc. as capsules containing 40 mg, 80 mg and 125 mg of aprepitant for oral administration. Aprepitant was developed and is currently marketed as a nanoparticle formulation to overcome its poor solubility/permeability characteristics. See, e.g., U.S. Pat. No. 5,145,684. But even with a nanoparticulate formulation, the mean absolute bioavailability of aprepitant is still only 60-65%.

There is a need therefore to develop new forms of aprepitant that have improved dissolution, solubility and/or increased bioavailability. The aprepitant composition and cocrystal of this invention answers such needs.

Although therapeutic efficacy is the primary concern for an active pharmaceutical ingredient (API), the salt and solid state form (i.e., the crystalline or amorphous form) of a drug candidate can be critical to its pharmacological properties, such as bioavailability, and to its development as a viable API. Recently, crystalline forms of API's have been used to alter the physicochemical properties of a particular API. Each crystalline form of a drug candidate can have different solid state (physical and chemical) properties. The differences in physical properties exhibited by a novel solid form of an API (such as a cocrystal or polymorph of the original therapeutic compound) affect pharmaceutical parameters such as storage stability, compressibility and density (important in formulation and product manufacturing), and solubility and dissolution rates (important factors in determining bioavailability). Because these practical physical properties are influenced by the solid state properties of the crystalline form of the API, they can significantly impact the selection of a compound as an API, the ultimate pharmaceutical dosage form, the optimization of manufacturing processes, and absorption in the body. Moreover, finding the most adequate solid state form for further drug development can reduce the time and the cost of that development.

Obtaining crystalline forms of an API is extremely useful in drug development. It permits better characterization of the drug candidate's chemical and physical properties. It is also possible to achieve desired properties of a particular API by forming a cocrystal of the API and a coformer. Crystalline forms often have better chemical and physical properties than the free base in its amorphous state. Such crystalline forms may, as with the cocrystal of the invention, possess more favorable pharmaceutical and pharmacological properties or be easier to process than known forms of the API itself. For example, a cocrystal may have different dissolution and solubility properties than the API itself and can be used to deliver APIs therapeutically. New drug formulations comprising a cocrystal of a given API may have superior properties over its existing drug formulations. They. may also have better storage stability.

Another potentially important solid state property of an API is its dissolution rate in aqueous fluid. The rate of dissolution of an active ingredient in a patient's stomach fluid may have therapeutic consequences since it impacts the rate at which an orally administered active ingredient may reach the patient's bloodstream.

A cocrystal of an API is a distinct chemical composition of the API and coformer(s) and generally possesses distinct crystallographic and spectroscopic properties when compared to those of the API and coformer(s) individually. Crystallographic and spectroscopic properties of crystalline forms are typically measured by X-ray powder diffraction (XRPD) and single crystal X-ray crystallography, among other techniques. Cocrystals often also exhibit distinct thermal behavior. Thermal behavior is measured in the laboratory by such techniques as capillary melting point, thermogravimetric analysis (TGA) and differential scanning calorimetry (DSC).

SUMMARY OF THE INVENTION

The invention relates to a 1:1:1 aprepitant L-proline hydrate composition and a 1:1:1 aprepitant L-proline $H_2O$ cocrystal as well as pharmaceutical compositions containing it and a pharmaceutically acceptable carrier. The cocrystal has a better dissolution rate than does aprepitant. The 1:1:1 aprepitant L-proline $H_2O$ composition and cocrystal may be used in the same way as aprepitant to treat or prevent disorders relating to emesis, a neuropsychiatric disease, an inflammatory disease, pain, cancer, a skin disease, itch, a respiratory disease, or an addiction,

BRIEF DESCRIPTION OF FIGURES

FIG. 1 shows an XRPD pattern for the 1:1:1 aprepitant L-proline $H_2O$ cocrystal.

FIG. 2 shows an ORTEP drawing of Molecule A of the 1:1:1 aprepitant L-proline $H_2O$ cocrystal at 100 K.

FIG. 3 shows an ORTEP drawing of Molecule B of the 1:1:1 aprepitant L-proline $H_2O$ cocrystal at 100 K.

FIG. 4 shows a packing diagram of the 1:1:1 aprepitant L-proline $H_2O$ cocrystal at 100K.

FIG. 5 shows a calculated XRPD pattern for the 1:1:1 aprepitant L-proline $H_2O$ cocrystal at 100K.

FIG. 6 shows an ORTEP drawing of the 1:1:1 aprepitant L-proline $H_2O$ cocrystal at 294 K.

FIG. 7 shows a packing diagram of the 1:1:1 aprepitant L-proline $H_2O$ cocrystal at 294 K.

FIG. 8 shows a calculated XRPD pattern for the 1:1:1 aprepitant L-proline $H_2O$ cocrystal at 294 K.

FIG. 9 shows a DSC trace for the 1:1:1 aprepitant L-proline $H_2O$ cocrystal.

FIG. 10 shows a TGA trace for the 1:1:1 aprepitant L-proline $H_2O$ cocrystal.

FIG. 11 shows the $^1H$ NMR spectrum of 1:1:1 aprepitant L-proline $H_2O$ cocrystal.

FIG. 12 shows the $^{13}C$ solid state NMR spectrum of the 1:1:1 aprepitant L-proline $H_2O$ cocrystal recorded using dipolar dephasing.

FIG. 13 shows the mean dissolution profiles, over the first 30 minutes, for the 1:1:1 aprepitant L-proline $H_2O$ cocrystal and crystalline aprepitant in distilled water containing 2.2% SDS.

FIG. 14 shows an overlay of the XRPD patterns of the 1:1:1 aprepitant L-proline $H_2O$ cocrystal at various time points during a 6 month accelerated stability study at 40° C./75% RH.

DETAILED DESCRIPTION

The invention relates to improvements of the physiochemical and/or the pharmaceutical properties of aprepitant. Disclosed herein is a new aprepitant composition, 1:1:1 aprepitant L-proline hydrate and a cocrystal of aprepitant, a 1:1:1 aprepitant L-proline $H_2O$ cocrystal. The cocrystal has an improved dissolution rate over crystalline aprepitant itself and does not require formulation as nanoparticles. The therapeutic uses of this aprepitant cocrystal are described below as well as therapeutic compositions containing the cocrystal. The cocrystal and the methods used to characterize it are described below.

Therapeutic Uses of the Aprepitant Composition and Cocrystal

The invention further relates to the therapeutic use of the aprepitant composition and cocrystal of the invention, 1:1:1 aprepitant L-proline $H_2O$ cocrystal, to treat or prevent emesis, e.g., vomiting and/or nausea as discussed above. The aprepitant composition or cocrystal of the invention may be also used to treat neuropsychiatric diseases, inflammatory diseases, pain (including migraine), cancers, skin diseases, itch, asthma and other respiratory diseases, addiction disorders such as alcoholism, also discussed above. Accordingly, the invention relates to method of treating such a disorder comprising the step of administering to a patient in need thereof a therapeutically effective amount of 1:1:1 aprepitant L-proline $H_2O$ or of administering to a patient in need thereof a therapeutic composition containing the aprepitant composition or cocrystal of the invention.

The term "treatment" or "treating" means any treatment of a condition or disorder in a mammal, including: preventing or protecting against the condition or disorder, that is, causing the clinical symptoms not to develop; inhibiting the condition or disorder, that is, arresting or suppressing the development of clinical symptoms; and/or relieving the condition or disorder (including the relief of discomfort associated with the condition or disorder), that is, causing the regression of clinical symptoms. It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" the condition or disorder. The term "protection" is meant to include "prophylaxis."

Pharmaceutical Compositions Containing the Aprepitant Composition and Cocrystal

The invention also relates to pharmaceutical compositions comprising a therapeutically effective amount of a 1:1:1 aprepitant L-proline $H_2O$ composition or cocrystal according to the invention and a pharmaceutically acceptable carrier (also known as a pharmaceutically acceptable excipient). As mentioned above, these pharmaceutical compositions are therapeutically useful to treat or prevent disorders, such as those discussed above, relating to emesis, a neuropsychiatric disease, an inflammatory disease, pain, cancer, a skin disease, itch, a respiratory disease, or an addiction.

A pharmaceutical composition of the invention may be in any pharmaceutical form which contains the 1:1:1 aprepitant L-proline $H_2O$ composition or cocrystal according to the invention. The pharmaceutical composition may be, for example, a tablet, capsule, liquid suspension, injectable, topical, or transdermal. Liquid pharmaceutical compositions may be prepared comprising the 1:1:1 aprepitant L-proline hydrate of the invention. The pharmaceutical compositions generally contain, for example, about 1% to about 99% by weight of the 1:1:1 aprepitant L-proline $H_2O$ composition or cocrystal of the invention and, for example, 99% to 1% by weight of at least one suitable pharmaceutical excipient. In one embodiment, the composition may be between about 5% and about 75% by weight of the 1:1:1 aprepitant L-proline $H_2O$ composition or cocrystal of the invention with the rest being at least one suitable pharmaceutical excipient or at least one other adjuvant, as discussed below.

A "therapeutically effective amount of the 1:1:1 aprepitant L-proline $H_2O$ composition or cocrystal according to the invention" is that which correlates to about 25-about 250 mg of aprepitant itself. As discussed above, aprepitant is marketed as 40 mg, 80 mg and 125 mg capsules or a 115 mg injectable by Merck & Co., Inc. under the Emend® tradename. The Emend® product is prescribed to prevent first-day nausea and vomiting related to chemotherapy and continues to prevent delayed nausea that can occur up to 5 days after treatment. Typical doses are about 125 mg 1 hour before chemotherapy on day 1, then 80 mg 1 hour before chemotherapy on days 2 and 3. EMEND® prescribing information.

The actual amount required for treatment of any particular condition or disorder or any particular patient may depend upon a variety of factors including, for example, the disease state being treated and its severity; the specific pharmaceutical composition employed; the age, body weight, general health, sex and diet of the patient; the mode of administration; the time of administration; the route of administration; and the rate of excretion of aprepitant; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001, which is incorporated herein by reference.

Depending on the type of pharmaceutical composition, the pharmaceutically acceptable carrier may be chosen from any one or a combination of carriers known in the art. The choice of pharmaceutically acceptable carrier depends upon the pharmaceutical form and the desired method of administration to be used. For a pharmaceutical composition of the invention, that is one having the 1:1:1 aprepitant L-proline $H_2O$ cocrystal of the invention, a carrier should be chosen that maintains the crystalline form. In other words, the carrier should not substantially alter the 1:1:1 aprepitant L-proline $H_2O$ cocrystal. Nor should the carrier be otherwise incompatible with the 1:1:1 aprepitant L-proline $H_2O$ cocrystal used, such as by producing any undesirable biological effect or otherwise interacting in a deleterious manner with any other component(s) of the pharmaceutical composition. Because, as shown by the dissolutions study below, once dissolved the 1:1:1 aprepitant L-proline $H_2O$ cocrystal remains in solution with no re-precipitation of aprepitant, the 1:1:1 aprepitant L-proline hydrate composition of the invention may be use to prepare liquid formulations of aprepitant.

The pharmaceutical compositions of the invention may be prepared by methods know in the pharmaceutical formulation art, for example, see Remington's Pharmaceutical Sciences, 18th Ed., (Mack Publishing Company, Easton, Pa., 1990), which is incorporated herein by reference. In a solid dosage form, the 1:1:1 aprepitant L-proline $H_2O$ cocrystal may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, aliginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like, (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents. Other formulations suitable for oral administration may be in the form of discrete units as capsules, sachets, or lozenges, in the form of a powder or granules; in the form of a solution or a suspension in an aqueous liquid or non-aqueous liquid, such as ethanol or glycerol; or in the form of an oil-in-water emulsion or a water-in-oil emulsion. A bolus, electuary or paste may also be relevant. Suitable oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone.

Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents, and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Liquid dosage forms may be aqueous, may contain a pharmaceutically acceptable solvent as well as traditional liquid dosage form excipients known in the art which include, but are not limited to, buffering agents, flavorants, sweetening agents, preservatives, and stabilizing agents.

Compositions for rectal administrations are, for example, suppositories that may be prepared by mixing the 1:1:1 aprepitant L-proline $H_2O$ cocrystal with, for example, suitable non-irritating excipients or carriers such as cocoa butter, polyethyleneglycol or a suppository wax, which may be solid at ordinary temperatures but may be liquid at body temperature and, therefore, melt while in a suitable body cavity and release the active component therein.

Compositions suitable for topical administration include liquid or semi-liquid preparations such as liniments, lotions, gels, applicants, oil-in-water or water-in-oil emulsions such as creams, ointments, pastes or foams; or solutions or suspensions such as drops, as is known in the art. Composition of the invention intended for topical administration, in which case the carrier may suitably comprise a solution, emulsion, ointment or gel base. The carrier or base, for example, may comprise one or more of the following: petrolatum, lanolin, polyethylene glycols, bee wax, mineral oil, diluents such as water and alcohol, and emulsifiers and stabilizers Thickening agents may be present in a pharmaceutical composition for topical administration. if intended for transdermal administration, the composition may include a transdermal patch or iontophoresis device. Topical formulations may contain a concentration of the compound of the invention from about 0.1 to about 10% w/v (weight per unit volume).

Because the 1:1:1 aprepitant L-proline $H_2O$ cocrystal may be maintained during preparation, solid dosage forms are preferred for the pharmaceutical composition of the invention. Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier). The 1:1:1 aprepitant L-proline $H_2O$ composition and cocrystal according to the invention may also be used as to formulate liquid or injectable pharmaceutical compositions. Administration of the 1:1:1 aprepitant L-proline $H_2O$ compound or cocrystal in pure form or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, intrasystemically, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the condition to be treated.

EXAMPLES

The following analytical methods were used to characterize the 1:1:1 aprepitant L-proline $H_2O$ cocrystal of the invention:

X-ray Powder Diffraction Characterization: X-ray powder diffraction patterns for the samples were acquired on a Bruker D8 diffractometer using CuKα radiation (40 kV, 40 mA), θ-2θ goniometer, V4 receiving slits, a Ge monochromator and a Lynxeye detector. The instrument is performance checked using a certified Corundum standard (NIST 1976). The data were collected at ambient temperature over an angular range of 2° to 42° 2θ using a step size of 0.05° 2θ and a step time of 0.5 seconds. Samples run under ambient conditions were prepared as flat plate specimens using powder as received without grinding. Approximately, 35 mg of the sample was gently packed into a cavity cut into polished, zero background (510) silicon wafer. All samples were analysed using Diffrac Plus EVA v11.0.0.2 or v13.0.0.2.

Single Crystal X-Ray Diffraction (SCXRD): Data were collected on an Oxford Diffraction SuperNova Dual source, Cu at zero, Atlas CCD Diffractometer equipped with an Oxford Cryosystems Cryostream cooling device. Structures were solved using the Bruker SHELXTL program and refined with the SHELXTL program as part of the Bruker SHELXTL suite. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Thermal Analysis—Differential Scanning calorimetry (DSC): DSC data was collected on a TA instruments Q2000 equipped with a 50 position autosampler. The calibration for thermal capacity was carried out using sapphire and the calibration for the energy and temperature was carried out using certified indium. Typically 0.8-1.2 mg of each sample, in a pin-holed aluminium pan, was heated at 10° C./min from 25'C to 350° C. A purge of dry nitrogen at 50 ml/min was maintained over the sample. The instrument control software was Advantage for Q series v2.8.0.392 and Thermal Advantage v4.8.3. All data analysis was performed using Universal Analysis v4.3A software.

Thermo-Gravimetric Analysis (TGA): TGA data were collected on a TA Instruments Q500 TGA, equipped with a 16 position auto-sampler. The instrument was temperature calibrated using certified Alumel. Typically 5-30 mg of each sample was loaded onto a pre-tared platinum crucible and aluminium DSC pan, and was heated at 10° C./min from ambient temperature to 350° C. A nitrogen purge at 60 ml/min was maintained over the sample. The instrument control software was Advantage for Q Series v2.8.0.392 and Thermal Advantage v4.8.3

Solution Proton NMR: $^1$H-NMR spectra were recorded on a Bruker 400 MHz spectrometer equipped with an auto-sample/and controlled by a DRX400 console. The samples were dissolved in d6-DMSO for analysis. The data was acquired using ICON-NMR v4.0.4 (build 1) running with Topspin v1.3 (patch level 8) using the standard Bruker loaded experiments.

Water Determination by Karl Fischer Titration (KF): The water content of each sample was measured on a Mettler Toledo DL39 Coulometer using Hydranal Coulomat AG reagent and an argon purge. Weighed solid samples were introduced into the vessel on a platinum TGA pan which was connected to a subaseal to avoid water ingress. Approx 10 mg of sample was used per titration and triplicate determinations were made.

$^{13}$C Solid State NMR: The $^{13}$C NMR spectra were obtained at ambient temperature using a Varian VNMRS spectrometer operating at 100.56 MHz for $^{13}$C and a 6 mm (rotor o.d.) magic-angle spinning probe. Spectra were acquired at ambient temperature using a proton decoupled cross-polarisation magic angle spinning experiment and under the acquisition conditions of recycle 3.5 s, contact time 5 ms and at a spin rate of 6.8 KHz. The spectra were recorded using "dipolar dephasing" spectral editing with a dephasing delay of 50 µs. The spectral referencing was with respect to neat, external tetramethylsilane (by setting the high frequency line from adamantane to 38.5 ppm).

Stability Study X-Ray Powder Diffraction Characterisation: X-Ray Powder Diffraction patterns at the required time points were collected on a PANalytical diffractometer using Cu Kα radiation (45 kV, 40 mA), θ-θ goniometer, focusing mirror, divergence slit (½"), soller slits at both incident and divergent beam (4 mm) and a PIXcel detector. The software used for data collection was X'Pert Data Collector, version 2.2f and the data was presented using X'Pert Data Viewer, version 1.2d. Instrument verification was performed using a silicon and benzoic acid standard, performed with the same batch program as listed below for sample analysis. Samples were run under ambient conditions and were analysed by transmission foil XRPD, using the powder as received. Approximately 2-5 mg of the sample was mounted on a 96 position sample plate supported on a polyimide (Kapton, 12.7 µm thickness) film. Plate height (Z) was set to 9 mm. Data was collected in the range 3-40° 2θ with a continuous scan (speed of 0.2° 2θ/s).

Example 1

1:1:1 Aprepitant L-proline H$_2$O Cocrystal 1.1 Preparation of a 1:1:1 Aprepitant L-proline H$_2$O Cocrystal The batch of the 1:1:1 aprepitant L-proline H$_2$O cocrystal used for characterisation was prepared as follows:

Aprepitant (300 mg) and L-proline (64.6 mg) were weighed into a glass vial. Nitromethane (1.5 ml) was added to the vial. The resulting slurry was placed in a shaker and matured for 5 days (RT to 50° C. on an 8 hour cycle, heating to 50° C. for 4 hours and then cooling to RT for a further 4 hours). The product was then filtered under vacuum and the resulting crystals dried in a vacuum oven at 40° C. overnight.

1.2 XRPD Characterisation of a 1:1:1 Aprepitant L-proline H$_2$O Cocrystal

The experimental XRPD pattern of the 1:1:1 aprepitant L-proline H$_2$O cocrystal is shown in FIG. 1. Table 1 lists the angles, °2θ±0.2°2θ, and d-spacing of the peaks identified in the experimental XRPD pattern of FIG. 1. The entire list of peaks, or a subset thereof, may be sufficient to characterize the cocrystal. For example, the cocrystal may be characterised by at least three peaks selected from the peaks at 6.4, 9.4, 11.9, 12.9, 14.6, and 18.8°2θ±0.2°2θ as well as by a XRPD pattern substantially similar to FIG. 1.

TABLE 1

| Angle °2θ ± 0.2 °2θ | d value Angstrom | Intensity % |
|---|---|---|
| 6.4 | 13.80 | 27.90 |
| 7.6 | 11.65 | 9.80 |
| 9.4 | 9.37 | 28.30 |
| 10.0 | 8.83 | 6.20 |
| 11.9 | 7.45 | 96.80 |
| 12.2 | 7.22 | 10.10 |
| 12.9 | 6.88 | 37.30 |
| 13.5 | 6.55 | 23.70 |
| 13.8 | 6.42 | 12.90 |
| 14.6 | 6.05 | 70.90 |
| 15.3 | 5.80 | 22.60 |
| 16.1 | 5.50 | 6.70 |
| 16.8 | 5.27 | 6.40 |
| 17.5 | 5.06 | 40.50 |
| 18.0 | 4.91 | 47.50 |
| 18.8 | 4.70 | 31.60 |
| 19.4 | 4.58 | 96.50 |
| 20.0 | 4.43 | 62.10 |
| 20.6 | 4.32 | 82.60 |
| 21.2 | 4.18 | 100.00 |
| 21.5 | 4.12 | 18.90 |
| 21.7 | 4.10 | 15.70 |
| 22.8 | 3.90 | 17.10 |
| 23.1 | 3.85 | 16.30 |
| 23.4 | 3.81 | 22.50 |
| 23.7 | 3.75 | 10.00 |
| 24.0 | 3.70 | 9.00 |
| 24.3 | 3.66 | 20.90 |
| 24.7 | 3.60 | 17.40 |
| 24.9 | 3.57 | 10.00 |
| 25.7 | 3.46 | 6.20 |
| 25.9 | 3.43 | 12.20 |
| 26.4 | 3.38 | 13.00 |
| 26.9 | 3.31 | 16.00 |
| 27.2 | 3.28 | 6.00 |
| 27.7 | 3.22 | 9.50 |
| 28.1 | 3.17 | 6.40 |
| 28.4 | 3.14 | 5.80 |
| 29.2 | 3.05 | 6.00 |
| 29.5 | 3.03 | 12.60 |
| 30.1 | 2.97 | 8.60 |
| 30.8 | 2.90 | 7.30 |
| 31.7 | 2.82 | 11.70 |
| 32.2 | 2.77 | 5.50 |
| 32.4 | 2.76 | 6.40 |
| 33.3 | 2.69 | 5.60 |
| 34.0 | 2.64 | 8.60 |
| 34.8 | 2.58 | 9.00 |
| 35.5 | 2.52 | 8.50 |
| 36.0 | 2.49 | 5.50 |
| 36.7 | 2.45 | 5.10 |
| 37.3 | 2.41 | 9.50 |
| 38.7 | 2.33 | 4.30 |
| 38.9 | 2.31 | 5.70 |
| 39.9 | 2.26 | 4.80 |

1.3 SCXRD Characterisation of a 1:1:1 Aprepitant L-proline H$_2$O Cocrystal

The crystal used for single crystal structure determination was prepared as follow:

Approximately 20 mg (estimated by eye) of the 1:1:1 aprepitant L-proline H$_2$O cocrystal batch prepared as previously described was placed in a glass HPLC vial and 1 ml of nitromethane was added. The sample was placed on a shaker at 50° C. for ca. 30 minutes before being removed and quickly filtered into a clean glass vial. The vial was covered with film which was then pierced to allow slow evaporation and crystal formation. A suitable single crystal was isolated from the crystals which formed by this method.

The single crystal data and structure refinement parameters for the structure measured at 100 K are reported in Table 2, below. There are two molecules of the 1:1:1 aprepitant L-proline H₂O cocrystal in the asymmetric unit of the crystal structure, labelled as Molecule A and Molecule B. ORTEP diagrams of the 1:1:1 aprepitant L-proline H₂O cocrystal for both Molecules A and B are shown in FIGS. 2 and 3 respectively. FIG. 2 is a view of molecule A of the 1:1:1 Aprepitant L-Proline H₂O Cocrystal at 100 K showing the numbering scheme employed. FIG. 3 is a view of molecule B of the 1:1:1 Aprepitant L-Proline H₂O Cocrystal at 100 K showing the numbering scheme employed. In FIGS. 2 and 3, anisotropic atomic displacement ellipsoids for the non-hydrogen atoms are shown at the 50% probability level. Hydrogen atoms are displayed with an arbitrarily small radius. A packing diagram for the 1:1:1 aprepitant L-proline H₂O cocrystal at 100 K, with hydrogen bonds shown as dashed lines, viewed down the a-axis of the unit cell is shown in FIG. 4.

The calculated XRPD pattern based on the single crystal data and structure for the 1:1:1 aprepitant L-proline H₂O cocrystal at 100 K is shown in FIG. 5. It is also noted that there are some small temperature shifts in some of the peaks owing to the fact that the experimental XRPD pattern was collected at room temperature and the calculated XRPD pattern is derived from data collected at 100 K. There are also small intensity differences owing to preferred orientation effects, present in the experimental pattern.

Slight differences can be observed between the ambient temperature experimental XRPD (FIG. 1) and the calculated XRPD pattern obtained from the single crystal data at 100 K (FIG. 5). A second SCXRD data set was collected on the 1:1:1 aprepitant L-proline H₂O cocrystal at ambient temperatures, e.g. at about 294 K.

The single crystal data and structure refinement parameters for the structure measured at 294 K are reported in Table 3, below. There is a single molecule of the 1:1:1 aprepitant L-proline H₂O cocrystal in the asymmetric unit of the crystal structure. An ORTEP diagram of the 1:1:1 aprepitant L-proline H₂O cocrystal is shown in FIG. 6. FIG. 6 is a view of molecule A of the 1:1:1 Aprepitant L-Proline H₂O Cocrystal at 294 K showing the numbering scheme employed. Anisotropic atomic displacement ellipsoids for the non-hydrogen atoms are shown at the 30% probability level. Hydrogen atoms are displayed with an arbitrarily small radius. A packing diagram for the 1:1:1 aprepitant L-proline H₂O cocrystal at 294 K, with hydrogen bonds shown as dashed lines, viewed down the a-axis of the unit cell is shown in FIG. 7.

Crystal data presented in Tables 2 and 3 may also be used to characterize the 1:1:1 aprepitant L-proline H₂O cocrystal of the invention. The cocrystal may be characterized by parameters such as its space group or its unit cell dimensions, e.g., by a $P2_12_12_1$ space group at a temperature of about 294 K; or unit cell dimensions of a=9.1963(4) Å, b=12.8332(9) Å, c=27.4289(19) Å, α=90°, β=90°, and γ=90° at a temperature of about 294 K.

The calculated XRPD pattern based on the single crystal data and structure for the 1:1:1 aprepitant L-proline H₂O cocrystal at 294 K is shown in FIG. 8. It is can be seen that in this case there is good agreement between the experimental XRPD pattern collected at room temperature and the calculated XRPD pattern is derived from data collected at 294 K. There are small intensity differences owing to preferred orientation effects present in the experimental pattern.

TABLE 2

| | |
|---|---|
| Molecular formula | $C_{28}H_{32}N_5O_6F_7$ |
| Molecular weight | 667.59 |
| Crystal System | Monoclinic |
| Space Group | $P2_1$ |
| Unit Cell Dimensions | a = 9.1229(2) Å |
| | b = 26.7988(5) Å |
| | c = 12.6369(2) Å |
| | α = 90° |
| | β = 92.826(2)° |
| | γ = 90° |
| Cell Volume | V = 3085.75(10) Å³ |
| Z | 4 |
| Temperature | 100(1) K |
| Radiation Wavelength/type | 1.54178/CuKα |
| Number of Reflections collected | 28161 |
| Number of observed Reflections, (I > 2σ(I)) | 26157 |
| Resolution, Max. 2θ, Completeness | 0.80 Å, 150.0°, 98.9% |
| wR² (all data) | 0.1176 |
| $R_1$ (I > 2σ(I)) | 0.0421 |
| Goodness of Fit | 1.007 |
| Flack parameter | −0.06(6) |
| Residual density (Max. Min.), eÅ⁻³ | 0.450, −0.367 |
| Morphology | Colourless Rod |

TABLE 3

| | |
|---|---|
| Molecular formula | $C_{28}H_{32}N_5O_6F_7$ |
| Molecular weight | 667.59 |
| Crystal System | Orthorhombic |
| Space Group | $P2_12_12_1$ |
| Unit Cell Dimensions | a = 9.1963(4) Å |
| | b = 12.8332(9) Å |
| | c = 27.4289(19) Å |
| | α = 90° |
| | β = 90° |
| | γ = 90° |
| Cell Volume | V = 3237.1(3) Å³ |
| Z | 4 |
| Temperature | 294(1) K |
| Radiation Wavelength/type | 1.54178/CuKα |
| Number of Reflections collected | 30624 |
| Number of unique reflections | 6588 |
| $R_{int}$ | 0.0427 |
| Number of observed Reflections, (I > 2σ(I)) | 5218 |
| Resolution, Max. 2θ, Completeness | 0.80 Å, 150.0°, 99.4% |
| wR² (all data) | 0.1875 |
| $R_1$ (I > 2σ(I)) | 0.0568 |
| Goodness of Fit | 1.005 |
| Flack parameter | 0.1(2) |
| Residual density (Max. Min.), eÅ⁻³ | 0.182, −0.169 |
| Morphology | Colorless Rod |

1.4 DSC of the 1:1:1 Aprepitant L-proline H₂O Cocrystal

The differential scanning calorimetry (DSC) trace obtained for the 1:1:1 aprepitant L-proline H₂O cocrystal is shown in FIG. 9. A broad endotherm is observed over the temperature range of 125-170° C. followed by an endotherm with an onset temperature of 220.9° C. and a peak maximum of 224.0° C.

1.5 TGA of the 1:1:1 Aprepitant L-proline H₂O Cocrystal

In the thermal gravimetric analysis (TGA) trace, FIG. 10, it can be seen that there is a weight loss of 2.7% over the temperature range of 100-190° C. which corresponds to one mole of water.

1.6 ¹H NMR Spectrum of the 1:1:1 Aprepitant L-proline H₂O Cocrystal

The ¹H NMR spectrum of the 1:1:1 aprepitant L-proline H₂O cocrystal, shown in FIG. 11, displays the following peaks: ¹H NMR (400 MHz, d6-DMSO) δ: 11.30 (1H), 7.86 (1H), 7.51 (2H), 7.37 (2H), 7.08 (2H), 4.94 (1H), 4.34 (1H), 4.12 (1H), 3.64 (1H), 3.49 (1H), 3.35 (1H), 3.21 (1H), 3.01 (1H), 2.83 (1H), 2.75 (1H), 2.39 (1H), 1.97 (2H), 1.73 (2H) and 1.36 (3H). The peak at 1.97 ppm in the ¹H NMR spectrum corresponds to two protons on the pyrrolidine ring of L-proline. Comparison of the integration of this peak with that at 7.86 ppm, which corresponds to one of the aromatic protons of aprepitant, indicates that the cocrystal has an aprepitant:L-proline stoichiometry of 1:1.

1.7 Karl Fischer Titration of the 1:1:1 Aprepitant L-proline $H_2O$ Cocrystal

Karl Fischer analysis of the 1:1:1 aprepitant L-proline $H_2O$ cocrystal indicated that the sample contained 2.9% water, which is equivalent to 1.1 mole of water, in agreement with the SCXRD structure showing that there is one molecule of water per API molecule in the cocrystal.

1.8 $^{13}C$ Solid State NMR Characterisation of a 1:1:1 Aprepitant L-proline $H_2O$ Cocrystal The $^{13}C$ solid state NMR spectrum of the 1:1:1 aprepitant L-proline $H_2O$ cocrystal, using dipolar dephasing, is shown in FIG. 12. The "dipolar dephasing" measurement leaves only signals from quaternary and methyl carbons, together with any associated spinning sidebands. Table 4 lists the characteristic shifts, ppm+/−0.5 ppm, observed in the experimental $^{13}C$ NMR spectrum of FIG. 12.

TABLE 4

| Chemical Shift ppm ± 0.500 ppm |
| --- |
| 175.7 |
| 161.2 |
| 158.2 |
| 148.0 |
| 145.7 |
| 133.2 |
| 132.2 |
| 131.5 |
| 123.8 |
| 24.3 |

1.9 Dissolution Study

The in vitro dissolution behaviour of the 1:1:1 aprepitant L-proline $H_2O$ cocrystal compared with that of pure crystalline aprepitant was examined in distilled water containing 2.2% SDS using the United States Pharmacopoeia Apparatus 2. Table 5 contains the full details of the method used. Material providing 125 mg of aprepitant was used in each dissolution experiment and in each experiment the test sample was added directly to the dissolution media as a loose powder.

TABLE 5

| | |
| --- | --- |
| Apparatus | USP Type II (paddle) |
| Dissolution medium | 2.2% SDS in purified water |
| Volume of media (ml) | 900 |
| Temperature of media | 37.0° C. ± 0.5° C. |
| Paddle speed (rpm) | 100 |
| Sampling Times (mins) | 1, 2, 3, 4, 5, 10, 15, 20, 30, 45, 60 |
| Infinity Time Point (mins) | 180 |
| Sampling Amount | 5 ml per time point |

Analysis was carried out by HPLC/UV using an Agilent 1100/1200 series HPLC system with UV variable wavelength detection. Details of the HPLC method used are shown in Table 6. Standards were prepared in acetonitrile at 0.14 mg/ml. All standard and sample solutions were filtered through 0.45 μm filters.

TABLE 6

| | |
| --- | --- |
| Mobile Phase A | 0.1% TFA in purified water |
| Mobile Phase B | 0.085% TFA in acetonitrile |
| Column | Phenomenex Luna C18 (2) 50 × 4.6 mm, 3 μm |
| Column Temperature | 25° C. |
| Flow Rate | 2.0 ml/min |

TABLE 6-continued

| | | | |
| --- | --- | --- | --- |
| Injection Volume | 5 μl | | |
| Wavelength | 260 nm | | |
| Run time | 4.4 minutes | | |
| | Time (min) | % A | % B |
| Gradient Program | 0 | 95 | 5 |
| | 1 | 80 | 20 |
| | 2.3 | 5 | 95 |
| | 3.3 | 5 | 95 |
| | 3.5 | 95 | 5 |
| | 4.4 | 95 | 5 |

The dissolution experiment was carried out in triplicate on both the 1:1:1 aprepitant L-proline $H_2O$ cocrystal and the pure aprepitant. The mean dissolution values obtained at the various time points are shown in Table 6. FIG. 13 illustrates the mean dissolution profiles observed for both the 1:1:1 aprepitant L-proline $H_2O$ cocrystal and the pure aprepitant over the first 30 minutes. It can be seen from Table 7 that under these test conditions more than 93% of the cocrystal had dissolved within one minute where as only 18.5% of the pure API had dissolved after this time. It was found that it took until almost the end of the dissolution experiment (180 minutes) for the pure crystalline aprepitant to achieve the same level of dissolution that the cocrystal achieved within the first minute of the study. This dissolution study showed that not only did the 1:1:1 aprepitant L-proline cocrystal demonstrate a rapid dissolution rate under these conditions but also that once dissolved the cocrystal remained in solution with no re-precipitation of the API under these conditions, which indicates that the 1:1:1 aprepitantL-proline-$H_2O$ cocrystal may be used to prepare liquid pharmaceutical formulations.

TABLE 7

| Time (mins) | 1:1:1 Aprepitant L-proline cocrystal (156 mg) | Crystalline Aprepitant (125 mg) |
| --- | --- | --- |
| 0 | 0.0 | 0.0 |
| 1 | 93.4 | 18.5 |
| 2 | 95.7 | 34.4 |
| 3 | 95.6 | 44.2 |
| 4 | 95.8 | 52.2 |
| 5 | 95.1 | 57.6 |
| 10 | 95.5 | 70.1 |
| 15 | 95.9 | 77.2 |
| 20 | 96.0 | 80.4 |
| 30 | 96.2 | 85.4 |
| 45 | 96.8 | 87.3 |
| 60 | 97.0 | 89.3 |
| 180 | 99.2 | 94.6 |

1.10: Stability Study

A stability study was carried out so as to examine the physical stability of the 1:1:1 aprepitant L-proline $H_2O$ cocrystal with respect to dissociation into its starting components over time under accelerated conditions. An equal quantity of the 1:1:1 aprepitant L-proline $H_2O$ cocrystal was placed in seven clear glass vials. The glass vials were loosely sealed with plastic screw caps so as to provide a barrier to solid transfer but to still allow moisture equilibration with the outer environment. The vial head space above the sample was estimated to be >95% of the total vial volume. All seven samples were then placed on a tray and stored within a stability cabinet set at 40° C./75% RH. The individual samples were pulled at pre-determined time points as shown in Table 8 and examined by XRPD. At every time point examined the XRPD pattern obtained was characteristic of the 1:1:1 aprepitant L-proline $H_2O$ cocrystal with no evidence of either of the starting materials. FIG. 14 illustrates the XRPD patterns obtained at the time points 0, three months and six months. FIG. 14 is an overlay of the XRPD patterns of the 1:1:1 aprepitant L-proline H$_2$O cocrystal at those time points during a 6 month accelerated stability study at 40° C./75% RH. It can be seen that there is no obvious change within the sample over the six month period and that there is no evidence of dissociation into either of the starting materials indicating that the 1:1:1 aprepitant L-proline H$_2$O cocrystal is stable under these conditions.

TABLE 8

| Time Point | XRPD Characterization |
|---|---|
| 0 | cocrystal |
| 1 week | cocrystal |
| 2 week | cocrystal |
| 3 week | cocrystal |
| 1 month | cocrystal |
| 2 months | cocrystal |
| 3 months | cocrystal |
| 6 months | cocrystal |

Example 2

Alternate Preparation of 1:1:1 Aprepitant L-proline H$_2$O Cocrystal

The 1:1:1 aprepitant L-proline H$_2$O cocrystal was also prepared as follows:

Aprepitant (500 mg) and L-proline (107.7 mg) were weighed into a glass vial. Acetonitrile (2.5 ml) and water (0.5 ml) were added to the vial. The resulting slurry was placed in a shaker and matured for 3 days (RT to 50° C. on an 8 hour cycle, heating to 50° C. for 4 hours and then cooling to RT for a further 4 hours). The product was then filtered under vacuum before being allowed to dry under ambient conditions overnight. XRPD analysis confirmed the product to be the same 1:1:1 aprepitant L-proline H$_2$O cocrystal.

The claimed invention is:

1. A 1:1:1 aprepitant L-proline H$_2$O cocrystal.
2. A 1:1:1 aprepitant L-proline H$_2$O cocrystal characterized by at least one of:
   a powder x-ray diffraction pattern having at least three peaks selected from the peaks at 6.4. 9.4, 11.9, 12.9, 14.6, 18.8, and °2θ±0.2°2 θ;
   a powder x-ray diffraction pattern substantially similar to FIG. 1;
   a P2$_1$2$_1$2$_1$ space group at a temperature of about 294 K; or unit cell dimensions of a =9.1963(4) Å, b =12.8332(9) Å, c =27.4289(19) ⊙, α=90°, β=90°, and γ=90° at a temperature of about 294 K.
3. A pharmaceutical composition comprising a 1:1:1 aprepitant L-proline H$_2$O cocrystal of claim 1 and a pharmaceutically acceptable carrier.
4. A method of treating disorders relating to emesis, a neuropsychiatric disease, an inflammatory disease, pain, cancer, a skin disease, itch, a respiratory disease, an addiction comprising the step of administering to a patient in need thereof a therapeutically effective amount of a 1:1:1 aprepitant L-proline H$_2$O cocrystal of claim 1.
5. A method of treating disorders relating to emesis, a neuropsychiatric disease, an inflammatory disease, pain, cancer, a skin disease, itch, a respiratory disease, an addiction comprising the step of administering to a patient in need thereof a therapeutically effective amount of a pharmaceutical composition of claim 3.
6. 1:1:1 aprepitant L-proline hydrate.
7. A pharmaceutical composition comprising 1:1:1 aprepitant L-proline hydrate of claim 6 and a pharmaceutically acceptable carrier.
8. A method of treating disorders relating to emesis, a neuropsychiatric disease, an inflammatory disease, pain, cancer, a skin disease, itch, a respiratory disease, an addiction comprising the step of administering to a patient in need thereof a therapeutically effective amount of 1:1:1 aprepitant L-proline hydrate of claim 6.
9. A method of treating disorders relating to emesis, a neuropsychiatric disease, an inflammatory disease, pain, cancer, a skin disease, itch, a respiratory disease, an addiction comprising the step of administering to a patient in need thereof a therapeutically effective amount of a pharmaceutical composition of claim 7.
10. A pharmaceutical composition comprising a 1:1:1 aprepitant L-proline H$_2$O cocrystal of claim 2 and a pharmaceutically acceptable carrier.
11. A method of treating or preventing disorders relating to emesis, a neuropsychiatric disease, an inflammatory disease, pain, cancer, a skin disease, itch, a respiratory disease, an addiction comprising the step of administering to a patient in need thereof a therapeutically effective amount of 1:1:1 aprepitant L-proline H$_2$O cocrystal of claim 2.
12. A method of treating disorders relating to emesis, a neuropsychiatric disease, an inflammatory disease, pain, cancer, a skin disease, itch, a respiratory disease, an addiction comprising the step of administering to a patient in need thereof a therapeutically effective amount of a pharmaceutical composition of claim 10.

* * * * *